(12) United States Patent
Bender et al.

(10) Patent No.: US 7,122,700 B2
(45) Date of Patent: Oct. 17, 2006

(54) ARYLAMINE PROCESSES

(75) Inventors: Timothy P. Bender, Ontario (CA); Nan-Xing Hu, Ontario (CA); H. Bruce Goodbrand, Ontario (CA)

(73) Assignee: Xerox Corporation, Stamford, CT (US)

( * ) Notice: Subject to any disclaimer, the term of this patent is extended or adjusted under 35 U.S.C. 154(b) by 139 days.

(21) Appl. No.: 10/909,136

(22) Filed: Jul. 30, 2004

(65) Prior Publication Data
US 2006/0025631 A1  Feb. 2, 2006

(51) Int. Cl.
C07C 209/68 (2006.01)
C07C 209/86 (2006.01)
C07C 209/78 (2006.01)

(52) U.S. Cl. ............ 564/305; 564/424; 564/425; 564/437; 564/438; 568/424

(58) Field of Classification Search .......... None
See application file for complete search history.

(56) References Cited

U.S. PATENT DOCUMENTS

| | | | |
|---|---|---|---|
| 3,929,836 A | 12/1975 | Hoffman-La Roche | |
| 3,996,215 A | 12/1976 | Kobayashi et al. | |
| 4,009,210 A | 2/1977 | Cahoy | |
| 4,093,812 A | 6/1978 | Rainer | |
| 4,157,333 A | 6/1979 | Nakatani et al. | |
| 4,226,792 A | 10/1980 | Tajima | |
| 4,317,774 A | 3/1982 | Sassiver et al. | |
| 4,343,938 A | 8/1982 | Sassiver et al. | |
| 4,455,427 A | 6/1984 | Johnson | |
| 4,457,939 A | 7/1984 | Schnur | |
| 4,490,531 A | 12/1984 | Johnson | |
| 4,495,357 A | 1/1985 | Johnson | |
| 4,661,636 A | 4/1987 | Englert et al. | |
| 4,755,613 A | 7/1988 | Thoer et al. | |
| 5,004,758 A | 4/1991 | Boem et al. | |
| 5,262,512 A | 11/1993 | Yanus et al. | |
| 5,281,578 A | 1/1994 | Bradley et al. | |
| 5,294,744 A | 3/1994 | Godek et al. | |
| 5,324,860 A | 6/1994 | Gao et al. | |
| 5,368,967 A | 11/1994 | Schank et al. | |
| 5,395,978 A | 3/1995 | Weisse et al. | |
| 5,436,099 A | 7/1995 | Schank et al. | |
| 5,571,649 A | 11/1996 | Mishra et al. | |
| 5,594,006 A | 1/1997 | Sakamoto et al. | |
| 5,599,988 A | 2/1997 | Mendelson | |
| 5,681,832 A | 10/1997 | Haugwitz et al. | |
| 5,693,807 A | 12/1997 | Sedelmeier et al. | |
| 5,725,986 A | 3/1998 | Grammatica et al. | |
| 5,849,798 A | 12/1998 | Charpentier et al. | |
| 5,863,685 A | 1/1999 | DeFeo et al. | |
| 5,976,746 A | 11/1999 | Tanaka et al. | |
| 6,034,256 A | 3/2000 | Carter et al. | |
| 6,077,850 A | 6/2000 | Carter et al. | |
| 6,083,943 A | 7/2000 | Ikunaka et al. | |
| 6,132,913 A | 10/2000 | Fuller et al. | |
| 6,150,412 A | 11/2000 | Pystynen et al. | |
| 6,194,450 B1 | 2/2001 | Charpentier et al. | |
| 6,207,334 B1 | 3/2001 | Dinh et al. | |
| 6,239,147 B1 | 5/2001 | Obach et al. | |
| 6,271,253 B1 | 8/2001 | Carter et al. | |
| 6,274,068 B1 | 8/2001 | Dimmit et al. | |
| 6,387,927 B1 | 5/2002 | Altmann et al. | |
| 6,458,423 B1 | 10/2002 | Goodson | |
| 6,492,390 B1 | 12/2002 | Carter et al. | |
| 6,495,300 B1 | 12/2002 | Qi et al. | |
| 6,515,003 B1 | 2/2003 | Pfahl et al. | |
| 6,573,016 B1 | 6/2003 | Kami et al. | |
| 6,627,367 B1 | 9/2003 | Tomiuchi et al. | |
| 6,686,507 B1 | 2/2004 | Watson et al. | |
| 6,732,864 B1 | 5/2004 | Usui | |
| 2002/0010206 A1 | 1/2002 | Carter et al. | |
| 2002/0025483 A1 | 2/2002 | Kawamura et al. | |
| 2002/0103141 A1 | 8/2002 | McKearn et al. | |
| 2002/0143182 A1 | 10/2002 | Pfahl et al. | |
| 2002/0177715 A1 | 11/2002 | Pesci et al. | |
| 2003/0036533 A1 | 2/2003 | Jomaa | |
| 2003/0045746 A1 | 3/2003 | Jamaa | |
| 2003/0083357 A1 | 5/2003 | Pfahl et al. | |
| 2003/0144329 A1 | 7/2003 | Pfal et al. | |
| 2003/0147670 A1 | 8/2003 | Asano et al. | |
| 2003/0153606 A1 | 8/2003 | Pfahl et al. | |
| 2003/0176741 A1 | 9/2003 | Watson et al. | |
| 2003/0208079 A1 | 11/2003 | Kunio | |
| 2003/0216432 A1 | 11/2003 | Pfahl et al. | |
| 2003/0232844 A1 | 12/2003 | Rogier, Jr. et al. | |
| 2004/0034004 A1 | 2/2004 | Pfahl et al. | |
| 2004/0038977 A1 | 2/2004 | Carter et al. | |
| 2004/0097566 A1 | 5/2004 | Pfahl et al. | |

FOREIGN PATENT DOCUMENTS

JP  2001/358158  12/2001

OTHER PUBLICATIONS

Smith, W., J. Org. Chem. (1972), 37(24), p. 3972-3973.*
Duff, J.C; J. Chem. Soc, 1941, 547-Abstract.
Pavlicic et al, Molecules 2002, 7 pp. 871-884.
Europ. J.Org. Chem. (2001), (15), 2947-2954.

(Continued)

Primary Examiner—Brian J. Davis
(74) Attorney, Agent, or Firm—Pillsbury Winthrop Shaw Pittman LLP

(57) ABSTRACT

A method for bisformylation an arylamine compound by reacting an arylamine compound with an alkyleneamine in a reaction mixture while refluxing an acid in the reaction mixture.

21 Claims, 1 Drawing Sheet

OTHER PUBLICATIONS

Synthesis, 8,543 (1975), "Improved Vilsmeer Haak procedure" Abstract.
Tetrahedron 49 (19) 4015-4034 (1993) "2,5-diamethoxybenzaldehyde" Abstract.
J.C.S. Perkins I,(1974) 1353-1354 "2,5-diamethoxybenzaldehyde" Abstract.
JCS Perkins I, (1980) 1862-1865 "Formylation of phenols with paraformaldehyde" Abstract.
JOC 37, 3972 (1972) "Assholium" Abstract.
Arch. Fharm, 308,p. 341- (1975) "Reimer-Tiemann formy;ations of 4-Methoxyphenol" Abstract.
Aldred, R., et al. "Magnesium-mediated ortho-Specific Formylation and Formaldoximation of Phenols," J. Chem. Soc. Perkin Trans. pp. 1823-1831 (1994).
Epstein, A.J., "Photo-and Electro- Luminescence Studies of Exciplex Emission at Polymer/ Polymer and Molecule/Molecule Interfaces," 4th Intl. Topical Conference (Feb. 2000).
Gustafson, T. L., et al., "The photophysics of phenyl disubstituted polyacetylenes: picosecond photoluminescence . . . ," Synthetic Metals vol. 116 pp. 31-34 (2001).
Organic Syntheses vol. 4 rev. ed. of annual vols. 30-39 "Indole-3-Aldehyde," pp. 539-542 (1963).
Kyllo, E.M., et al., "Photophysics of segmented block PPV copolymer derivatives," Synthetic Metals vol. 116 pp. 189-192 (2001).
March, J., "Advanced Organic Chemistry: Reactions, Mechanisms, and Structure," pp. 544-554 4th ed. (1992).
Tanner, et al., "Studies on a Chiral (N,P) Ligand Containing a C2-Symmetric Aziridine Unit," Acta Chemica Scandinavica vol. 53 No. 4 pp. 263-268 (1999).
Organic Reactions vol. 28 ch. 1 "The Reimer-Tiemann Reaction," pp. 1-37 (1982).

* cited by examiner

ARYLAMINE PROCESSES

BACKGROUND

Disclosed is a process for the generation of arylamine compounds. More specifically, illustrated herein are methods for bisformylating arylamines for synthesizing arylamine which can be incorporated into photoconductive imaging members as hole transport components.

Arylamines can be selected as hole transport molecules in organic photoconductors. Examples of arylamine hole transport molecules include a siloxane-containing hole transport molecule illustrated with reference to Compound I:

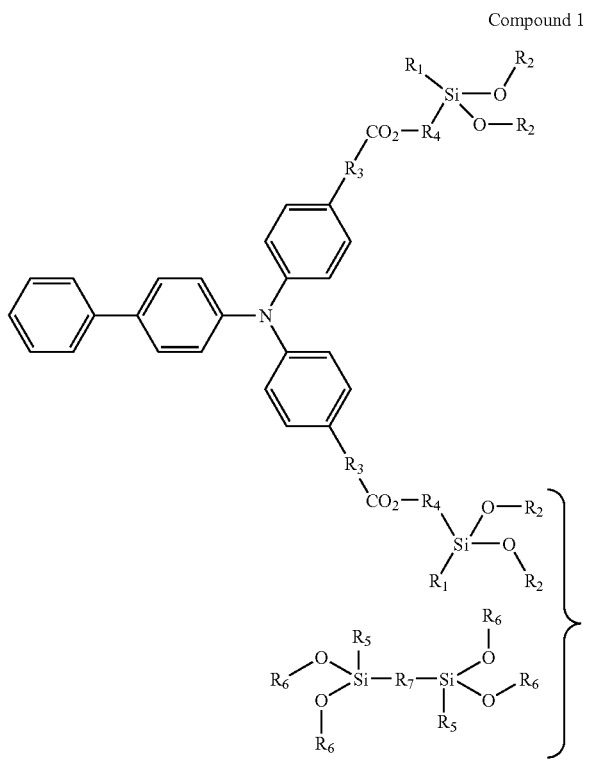

Compound I wherein $R_1$, $R_2$, $R_3$, $R_4$, $R_5$, $R_6$, and $R_7$, independently represent an alkyl or hydrocarbon radical of for example 1 to about 20 carbon atoms, such as methyl, ethyl, propyl, butyl, pentyl, stearyl, and higher analogs thereof.

Processes for preparing Compound I wherein $R_1$–$R_6$, are hydrocarbon radicals and more specifically where $R_2$ and $R_6$ are methyl, ethyl or isopropyl may be lengthy and involve reagents that may be considered not "environmentally friendly." For example, processes for preparing Compound I may entail as many as six distinct synthetic manipulations with up to 30 days to complete such manipulations, including a Vilsmeier reaction for the bisformylation of an intermediate Compound II (N,N-diphenyl-4-aminobiphenyl) to its bisformylated form.

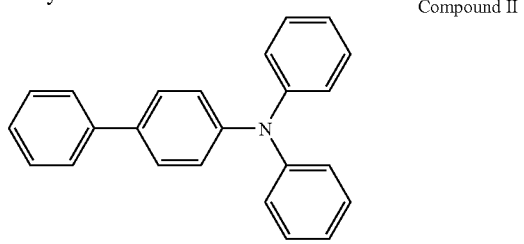

Compound II

The Vilsmeier reaction can be used to introduce aldehyde or formyl groups onto an aromatic ring to yield a formylated-aryl moiety. An example Vilsmeier reaction entails the formation of a Vilsmeier reagent which may be formed by reacting N,N-dimethylformamide (DMF) with phosphorous oxychloride ($POCl_3$), phosgene ($COCl_2$) or thionylchloride ($SOCl_2$) of which phosphorous oxychloride is preferred. The preparation of the Vilsmeier reagent is normally done in-situ. The Vilsmeier reagent then reacts with the aromatic ring of an activated molecule such as a phenol or aromatic amine. The introduction of such a group into a generic triarylamine is shown as the reaction sequence below:

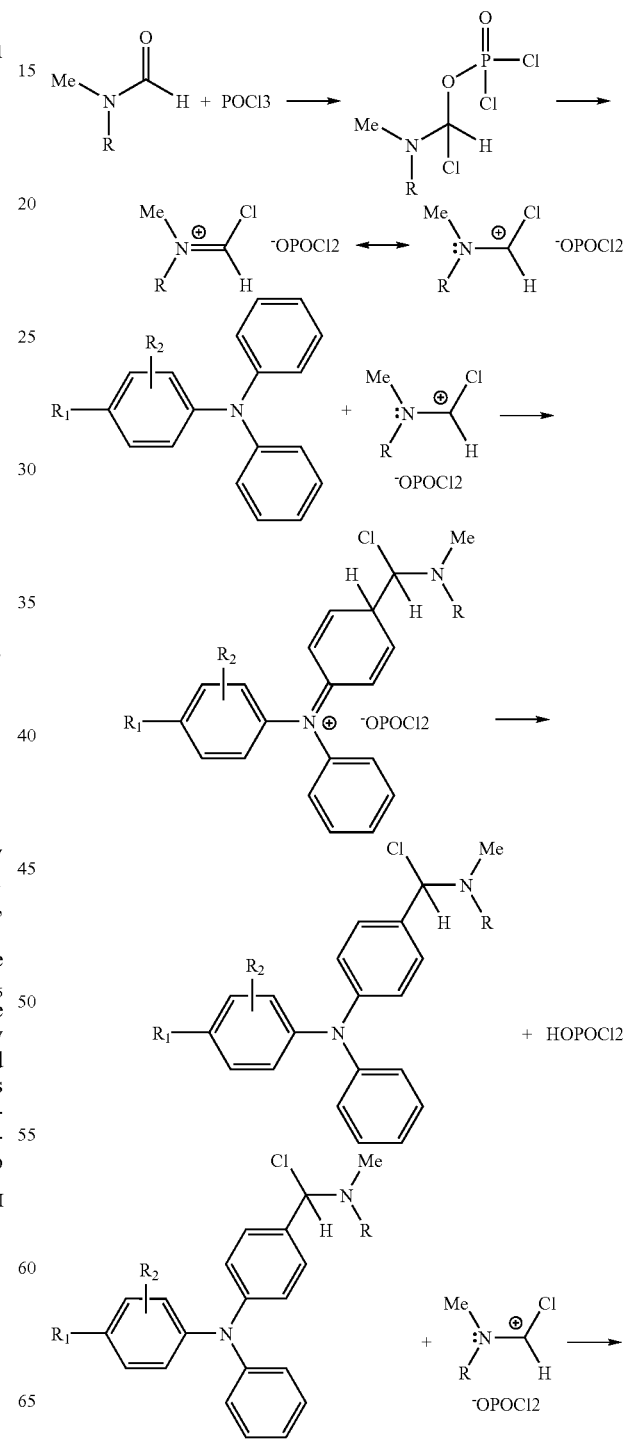

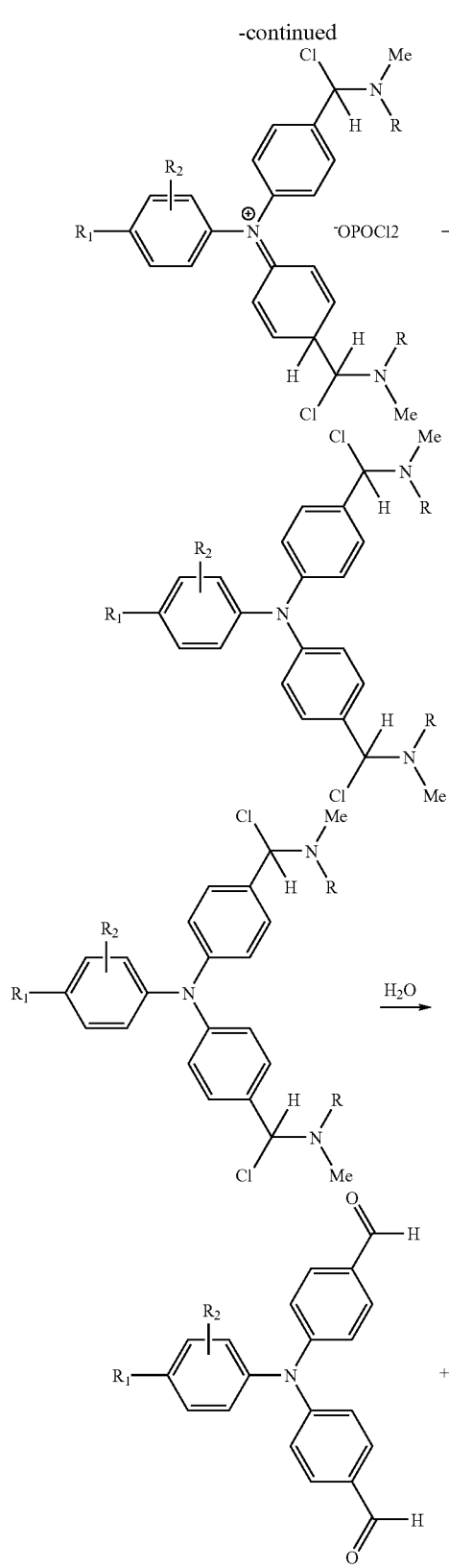

Compound II may be bisformylated by way of a Vilsmeier reaction as illustrated herein after. While monoformylation of Compound II may be achieved with relative ease by way of a Vilmeier reaction, bisformylation may be more difficult and may require that the reaction be accomplished at elevated temperatures of from about 90° C. to about 110° C., temperatures above the decomposition of the Vilsmeier reagent ($T_d$~81° C.). Another disadvantage to bisformylation of Compound II by the Vilsmeier reaction is that the reagents such as phosphorous oxychloride used in such a process may be considered to be hazardous and toxic.

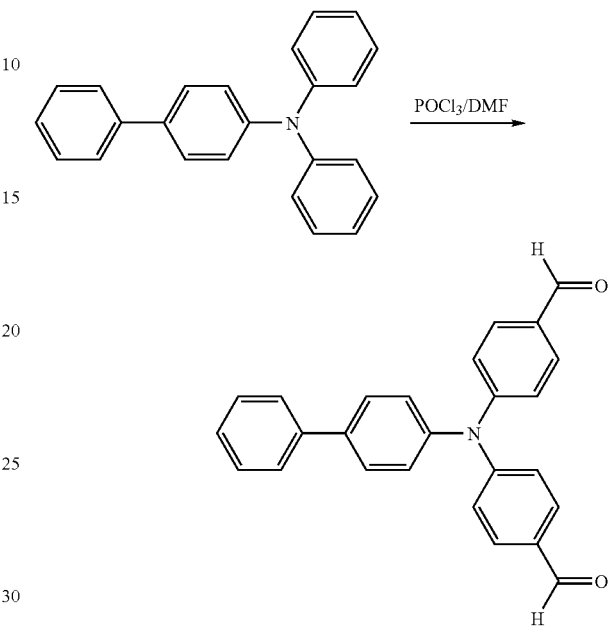

Bisformylation of Compound II Using a Vilsmeier Reaction

Additionally, bisformylation of Compound II by the Vilsmeier reaction may result in an intractable black tar that is neither organic nor aqueous soluble possibly due to the decomposition of the reactants, thus rendering working and cleaning difficult for the devices and equipment used in the process. Also, bisformylation of Compound II by the Vilsmeier reagent may result in conversion yields of less than 90%, for example from about 75 percent to about 85 percent.

Reaction schemes other than the Vilsmeier reaction that have been used for the introduction of aldehyde groups onto an aromatic ring include the Reimer-Tiemann Reaction (F. Reimer and F. Tiemann, Ber. 9, 824, 1268, 1285 (1876); H. Gilman, C. E. Arntzen and F. J. Webb, J. Org. Chem. 10, 374 (1945); L. N. Ferguson, Chem. Revs. 38, 229 (1946; Wynberg, Chem. Revs. 60, 169 (1960)), entailing the generation of dihalocarbene in situ, for example, by including chloroform and a hydroxide ion (⁻OH) or a base in the reaction mixture as follows:

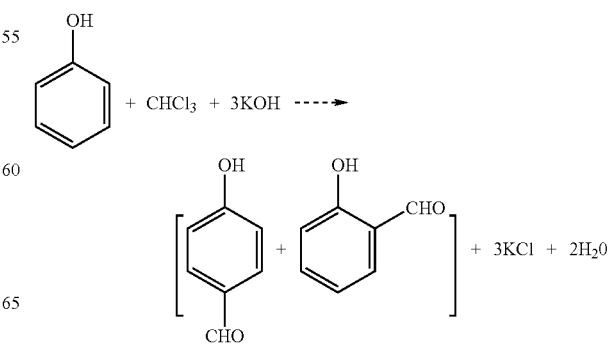

Exemplar Reimann-Tiemann Reaction and the Duff Reaction, employing an alkyleneamine such as hexamethylenetetraamine (HMTA) ($C_6H_{12}N_4$) in acidic ($H^+$) conditions. (See, in general, Duff, J. C.; J. Chem. Soc., 1941, 547; Lindoy, L. F.; Meehan, G. V.; Svenstrup, N.; Synthesis, 1998, 1029–1032; Smith, W. E.; J. Org. Chem., 1972, 37(24), 3972–3973; Allen, C. F. H.; Leubner, G. W.; Org. Syn. Coil. Vol. 3, 866; for example of synthetic utility of the reaction see: Larrow, J. F.; Jacobsen, E. N.; J. Org. Chem., 1994, 59, 1939–1942; for discussion of the mechanism of a Duff Reaction see: Ogata, Y.; Kawasaki, A.; Sugiura. F.; Tet. Lett., 1968, 24, 5001–5010).

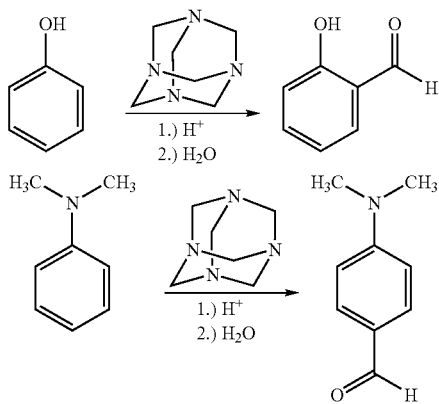

Exemplar Duff Reaction

The Reimer-Tiemann and Duff reactions may provide formylated-products, in low yields of from about 5 to about 50%.

There is, therefore, a need for processes that for example, result in a high yield of a bisformylated-arylamines and wherein such processes are designed to convert arylamines, such as Compound II, to bisformylated-arylamines. These processes may be useful in the synthesis of a number of siloxane-containing hole transport molecules.

SUMMARY

Aspects disclosed herein include
a method or process comprising reacting and refluxing an acid solution comprising an arylamine compound with from about 2 to about 200 molar equivalents of an alkyleneamine wherein the alkyleneamine may be hexamethylenetetraamine;
a method comprising reacting an arylamine compound with an alkyleneamine such as hexamethylenetetraamine in an acidic solution comprising 2 and about 200 molar equivalents of paraformaldehyde and/or 1,3,5-trioxane; and
a method comprising (a) providing or generating a bisulfite salt solution; (b) adding a composition mixture comprising a bisformyl-arylamine and a monoformyl-arylamine in an organic solvent to the bisulfite salt solution; (c) precipitating the bisformyl-arylamine by addition of the organic solvent to the bisulfite salt solution.

DETAILED DESCRIPTION

Figure 1:
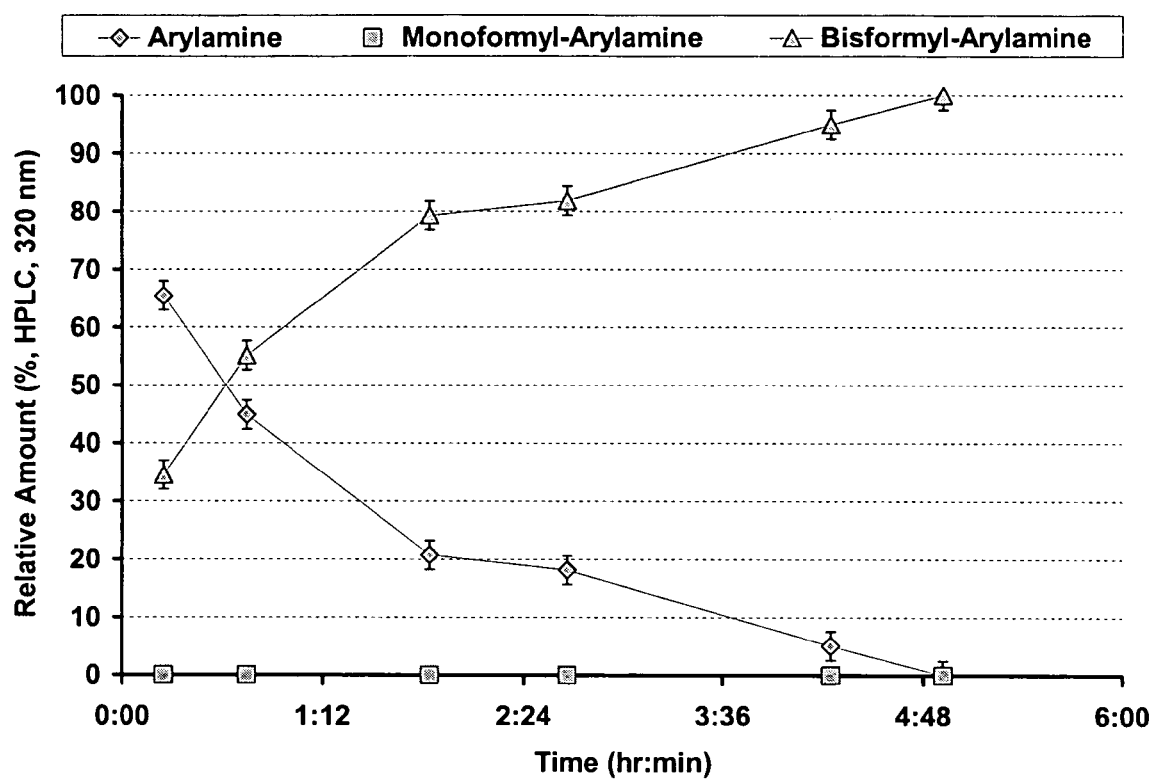
FIG. 1 is a time/conversion plot which illustrates the conversion of N,N-diphenyl-4-aminobiphenyl (Compound II) to bisformylated-Compound II using a modified Duff Reaction.

In embodiments there is illustrated:
a method for bisformylating arylamines comprising reacting an arylamine compound with from about 2 to about 200, from about 15 to about 100, or from about 25 to about 75 molar equivalents of an alkyleneamine wherein the alkyleneamine is hexamethylene tetraamine is for example, of the formula $C_6N_4H_{12}$ in a refluxing solution comprising an organic acid, for example trifluoroacetic acid.

The reaction may be accomplished at a temperature from about 20° C. to about 120° C., from about 50° C. to about 100° C. or from about 70° C. to about 90° C. depending on the boiling point of the organic acid or other components used. The acid amount selected may be equal to or more than about 1 mole equivalent per mole of formyl group to be added to the arylamine compound, for example, from about 1 to about 100, from about 1 to about 50, or from about 1 to about 25 molar equivalents. The acid to be refluxed may be an organic acid, an organic acid containing an inorganic acid, an organic solvent containing an organic acid, or an organic solvent containing an inorganic acid. For example, organic acids include, organic acids of the formula $RCO_3H$, wherein R is for example a straight chain or branched alkyl, such as methyl, propyl, isopropyl, butyl, isobutyl, pentyl, hexyl, heptyl, and octyl, and include, acetic acid, propionic acid, butanoic acid and the like, and may also include trifluoroacetic acid (TFA), perfluoropropionic acid, oxalic acid, methanesulfonic acid, and perfluorobutanoic or mixtures thereof. Inorganic acids that can be used in combination with an organic acid or an organic solvent include hydrogen bromide and hydrogen chloride, and examples of organic solvents include dimethylformamide and 1,4-dioxane. For example, an organic acid containing an inorganic acid include, hydrogen bromide in acetic acid, hydrogen bromide in TFA, hydrogen chloride in TFA and hydrogen bromide in butanoic acid. Examples of organic solvent containing an inorganic acid include hydrogen chloride in 1,4-dioxane, hydrogen bromide in 1,4-dioxane, hydrogen chloride in dimethylformamide and hydrogen bromide in dimethylformamide. Refluxing of the acid may aid in the bisformylation by accelerating the reaction and additionally may aid in the dissolution of the starting arylamine compound in the organic acid. The amount of alkyleneamine selected, may be from about 2 to about 200 molar equivalents, alternatively from about 2 to about 10 molar equivalents and alternatively from about 2 to about 5 molar equivalents, per mole of arylamine to be formylated. The alkyleneamine wherein alkyl is for example may be a polyamine, cyclic or non-cyclic, and may comprise hexamethylenetetramine (HTMA). The reaction may be accomplished at a temperature from about 20° C. to about 120° C., alternatively from about 70° C. to about 90° C.

Also, disclosed is a method for bisformylating arylamines comprising refluxing an acid, such as an organic acid, in a solution comprising hexamethylenetetramine ($C_6H_{12}N_4$, HMTA) in the presence of the arylamine at a temperature from about 20° C. to about 120° C.

The acid to be refluxed may be selected in non-catalytic quantities of for example, from about 1 to about 1,000, from about 2 to about 500, or from about 4 to about 100 molar equivalents to the number of formyl groups being introduced into the organic substrate. The acid to be refluxed may include at least one or mixtures of acetic acid, propionic acid, butanoic, trifluoroacetic acid (TFA), perfluoropropionic acid, perfluorobutanoic and methanesulfunic acid. The hexamethylenetetraamine ($C_6H_{12}N_4$, HTMA) concentration may be from about 2 to about 200 molar equivalents, alternatively from about 2 to about 10 molar equivalents, and alternatively from about 2 to about 5 molar equivalents per mole of arylamine to be converted to bis-arylamine.

The rate of bisformylation of the arylamines may be accelerated by inclusion of paraformaldehyde (polymeric formaldehyde) and/or 1,3,5-trioxane (cyclic formaldehyde) in the reaction mixture. Acceleration can be about 1.5 to about 10 times the reaction rate without the compounds especially when such compounds are present in a concentration of from about 2 to about 200 molar equivalents to the arylamine. Alternatively, the concentration of paraformaldehyde and/or 1,3,5-trioxane in the reaction mixture is from about 2 to about 40 molar equivalents, or from about 2 to about 5 molar equivalents per mole of arylamine.

A method that may be used for acceleration of bisformylation of arylamines comprises adding from about 2 molar equivalent to about 5 molar equivalents of one or more organic acids, such as acetic acid and trifluoroacetic acid, from about 2 molar equivalents to about 200 molar equivalents of an alkylalklyeneamine, such as hexamethylenetetraamine, and one or more accelerants, in a concentration from about 2 molar equivalents to about 5 molar equivalents, such an accelerant selected from the group consisting of 1,3,5-trioxane and paraformaldehyde, for every mole of starting arylamine compound, of for example arylamine compound II.

The bisformylated-arylamines obtained may be purified from monoformylated arylamines formed in the reaction process by precipitation from solution by forming a bisulfite adduct. An organic solution comprising bisformyl-arylamine/monoformyl-arylamine may be added to a bisulfite solution, which may be saturated, then the solution shaken. The salt that precipitates may be filtered and later washed with organic solvents, such as toluene. A dry powder may be formed. Free bisformyl-arylamine can be obtained by partitioning between toluene and saturated base solution, which may comprise bicarbonates, carbonates or hydroxides.

The bisformylation reactions may enable fewer safety concerns than associated with bisformylation reactions such as the Vilsmeier reaction in particular in respect of the reactants used in the reaction scheme.

Examples of arylamine compounds that can be produced in aspects illustrated herein include arylamine intermediates useful in the preparation of an arylamine hole transporting molecule such as N,N-bis(4-formylphenyl)-4-aminobiphenyl (Compound II) which may be prepared under the reaction conditions and using the amounts of reactants as described above.

The following Examples are provided.

EXAMPLE 1

Method for Bisformylation of N,N-diphenyl-4-aminobiphenyl (Compound II)

One mole of N,N-diphenyl-4-aminobiphenyl (Compound II) was refluxed as a solution in trifluoroacetic acid (TFA) in the presence of 4 molar equivalents of HMTA at a temperature of 20° C. and 120° C. Amounts of Compound II, monoformyl-Compound II and bisformyl-Compound II present in the reaction were measured over a six hour period using HPLC. A time/conversion plot was generated reference FIG. 1, the plot showing the relative amounts of each compound at different times.

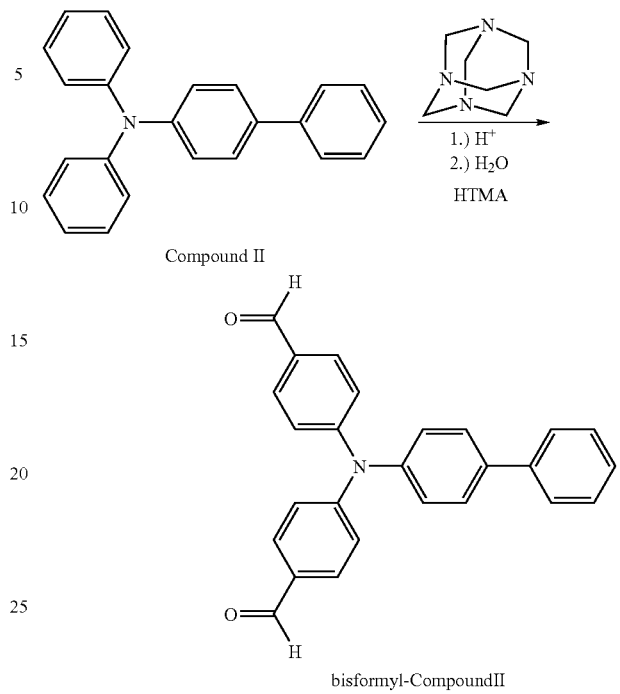

As illustrated in FIG. 1, bisformylated-Compound II was obtained in amounts greater than 80% at approximately 1.25 hr (hour) after incubation of the reaction mixture at temperatures ranging from about 85° C. to about 120° C., with complete conversion ($\geq$99%) of Compound II to its bisformylated form achieved in about 5 hours after the reaction has been terminated.

EXAMPLE 2

Effect of Acid Catalyst on Bisformylation of N,N-diphenyl-4-aminobiphenyl (Compound II) via Duff Reaction Acetic acid, propionic acid, hydrobromic acid in acetic acid, methanesulfonic acid, oxalic, trifluoroacetic acid (TFA), or boric acid and combinations thereof as shown under "conditions" in Table 1 were refluxed in a solution comprising Compound II and 2–4 molar equivalents of hexamethylenetetraamine (HTMA). The results of the conversion of Compound II to its mono- and bis-formylated form is shown in Table I as amount of Compound II (unformylated), amount of monoformyl-Compound II, and amount of bisformyl-Compound II measured after 3 hours at room temperature (about 20° C.), 2.5 hours at about 85° C., and overnight (from about 12 to about 16 hours) at 85° C. As illustrated in Table 1 below, TFA in quantities of from about 2 molar equivalents to about 4 molar equivalents permitted the bisformylation reaction of Compound II.

The data also suggest (sample numbers 1, 10 and 11) that from about 2 to about 4 molar equivalents of HMTA in the reaction mixture was sufficient to effect the bisformylation reaction in that 100% conversion of Compound II to its bisformylated form was accomplished at a temperature of 85° C., after 2.5 hours of incubation of the reaction mixture using TFA as the acid.

TABLE 1

| | Conditions | Reagent | 3 hrs r. t. | | | 2.5 hrs. - 85° C. | | | Overnight - 85° C. | |
|---|---|---|---|---|---|---|---|---|---|---|
| | | | CII | Monoformyl-CII | Bisformyl-CII | CII | Monoformyl-CII | Bisformyl-CII | CII | Monoformyl-CII |
| 1 | TFA | 1.16 g C6H12N4 (4 equiv.) | 94.52 | 1.23 | 4.26 | 0 | 0 | 100 | | |
| 2 | AcOH | 1.16 g C6H12N4 (4 equiv.) | 96.55 | 0 | 3.45 | 97.48 | 1.27 | 1.25 | 80.64 | 16.35 |
| 3 | PrCOOH | 1.16 g C6H12N4 (4 equiv.) | 95.87 | 0 | 4.13 | 95.26 | 0 | 4.74 | 98.33 | 0 |
| 4 | HBr/AcOH | 1.16 g C6H12N4 (4 equiv.) | 86.97 | 2.17 | 10.86 | | | | | |
| 5 | MeSO3H | 1.16 g C6H12N4 (4 equiv.) | 31.49 | 0 | 68.51 | | | | | |

| | Conditions | Reagent | 2.5 hrs - 85° C. | | | 5 hrs. - 85° C. | | | Overnight - 85° C. | |
|---|---|---|---|---|---|---|---|---|---|---|
| | | | CII | Monoformyl-CII | Bisformyl-CII | CII | Monoformyl-CII | Bisformyl-CII | CII | Monoformyl-CII |
| 6 | 1:1 TFA/AcOH | 1.16 g C6H12N4 (4 equiv.) | 0 | 35.17 | 64.83 | 0 | 27.5 | 72.5 | 0 | 15.24 |
| 7 | 1:3 TFA/AcOH | 1.16 g C6H12N4 (4 equiv.) | 2.6 | 84.97 | 12.42 | 0 | 83.63 | 16.37 | 0 | 81.53 |
| 8 | 0.1:3.9 TFA/AcOH | 1.16 g C6H12N4 (4 equiv.) | 95.07 | 1.92 | 3.01 | | | | 86.73 | 11.45 |
| 9 | 5 drops:4 mL TFA/AcOH | 1.16 g C6H12N4 (4 equiv.) | 95.06 | 1.99 | 2.95 | | | | 89.3 | 8.97 |
| 10 | TFA | 0.87 g C6H12N4 (3 equiv.) | 0 | 0 | 100 | | | | | |
| 11 | TFA | 0.58 g C6H12N4 (2 equiv.) | 0 | 0 | 100 | | | | | |
| 12 | 3.5 mL AcOH: 0.80 g oxalic acid | 1.16 g C6H12N4 (4 equiv.) | 70.51 | 26.65 | 2.83 | 68.83 | 28.43 | 2.74 | | |
| 13 | 3.5 mL AcOH: 0.525 g boric acid | 1.16 g C6H12N4 (4 equiv.) | 96.57 | 2.7 | 0.73 | | | | | |
| 14 | 3.5 mL ethylene glycol: 0.525 g boric acid | 1.16 g C6H12N4 (4 equiv.) | 98.51 | 0 | 1.41 | | | | | |

EXAMPLE 3

Acceleration of the Duff Reaction with Co-reagents

The effect of paraformaldehyde (polymeric formaldehyde) or 1,3,5-trioxane (cyclic formaldehyde) on the bisformylation of Compound II with 2.2–4 equivalents of hexamethylenetriamine (HTMA) refluxed with acetic acid and/or trifluoroacetic acid (TFA) and acetic acid and oxalic acid was investigated as set forth in Table 2. As seen in Table 2, either paraformaldehyde (polymeric formaldehyde) or 1,3,5-trioxane (cyclic formaldehyde) were found suitable reagents for accelerating the rate of the bisformylation reaction in mixtures refluxing acetic acid and TFA. By comparison with the baseline reaction conditions, the use of either reagent resulted in greater than 90% conversion to bisformyl-Compound II within 2.5 hrs compared to 64.8% for the baseline.

TABLE 2

| | | 2.5 hrs - 85° C. | | | 5 hrs - 85° C. | | |
|---|---|---|---|---|---|---|---|
| Conditions | Reagent | CII | Monoformyl-CII | Bisformyl-CII | CII | Monoformyl-CII | Bisformyl-CII |
| 1:1 TFA/AcOH | 1.16 g C6H12N4 (4 equiv.) | 0 | 35.17 | 64.83 | 0 | 27.5 | 72.5 |
| 3.5 mL | 1.16 g C6H12N4 (4 equiv.) | 70.51 | 26.65 | 2.83 | 68.83 | 28.43 | 2.74 |

TABLE 2-continued

|  | Conditions | Reagent | 2.5 hrs - 85° C. | | | 5 hrs - 85° C. | | |
|---|---|---|---|---|---|---|---|---|
|  |  |  | CII | Monoformyl-CII | Bisformyl-CII | CII | Monoformyl-CII | Bisformyl-CII |
|  | AcOH: 0.80 g oxalic acid | | | | | | | |
| 1 | 1:1 TFA/AcOH | 0.639 g C6H12N4 (2.2 equiv.) 0.411 g 1,3,5-trioxane | 5.53 | 0 | 94.47 | | | |
| 2 | 3.5 mL AcOH | 0.639 g C6H12N4 (2.2 equiv.) 0.411 g 1,3,5-trioxane 0.80 g oxalic acid | 60.48 | 26.08 | 13.44 | 6.59 | 74.58 | 18.82 |
| 3 | 1:1 TFA/AcOH | 0.639 g C6H12N4 (2.2 equiv.) 0.411 g paraformaldehyde | 3.99 | 0 | 96.01 | | | |
| 4 | 3.5 mL AcOH | 0.639 g C6H12N4 (2.2 equiv.) 0.411 g paraformaldehyde 0.80 g oxalic acid | 3.08 | 46.79 | 50.13 | 6.88 | 42.89 | 50.24 |

EXAMPLE 4

Purification of Bisformyl—Compound II by Bisulfite Adduct

The precipitate from Example 5 was dissolved in 100 ml toluene and treated in a Morton flask with 500 ml saturated sodium hydrogen sulfite (sodium bisulfite, freshly prepared) overnight (about 16 hours). The solid precipitate was filtered and washed with toluene. The solid was placed back in a Morton flask along with 250 ml saturated sodium bicarbonate and 250 ml toluene. The mixture was stirred for about 12 to 16 hrs. The phases were then separated. The toluene layer was dried by filtration through magnesium sulfate by gravity. The toluene was then removed to yield the product (75%, >98% purity by HPLC).

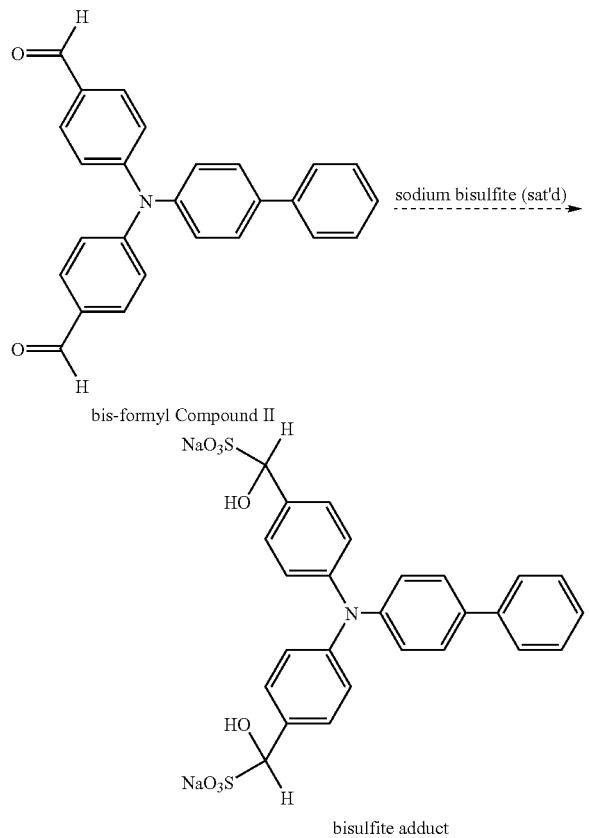

Alternatively, bisformyl-Compound II was separated from the precipitate by treatment with absorbents (activated clay or alumina) in hot toluene, resulting in an approximate yield of 85% when the crude material from Example 5 below was purified.

EXAMPLE 5

A Reaction Useful for Bisformylation of Compound II

To a 2 L 3-necked flask fitted with a mechanical stirrer, argon inlet/temperature controller and water condenser was charged in the following order: (a) 66.6 g Compound II; (b) 63.9 g hexamethylenetetraamine; (c) 41.1 g 1,3,5-trioxane; (d) 140 mL acetic acid (stirring startede); and (e) 140 mL trifluoroacetic acid.

The mixture was heated to 90° C. and then reduced to 60° C. according to the following temperature profile using a reactor control system: (a) from 55° C. to 75° C. in 10 minutes; (b) to 90° C. in 15 minutes; (c) held at 90° C. for 360 minutes; (d) reduced to 60° C. in 5 minutes with addition of 250 mL water (HPLC sample taken without workup to ensure complete hydrolysis); and (f) holding the mixture at 60° C. for 90 minutes.

The mixture was then transferred to a 2 L separatory funnel and, after cooling to room temperature, was twice extracted with toluene (2×250 mL). The combined toluene extracts were washed with water (250 mL) and then twice with saturated sodium chloride (2×250 mL). The toluene was dried by passing through a filter containing anhydrous magnesium sulfate and was removed by rotary evaporation. A crude yield of bisformylated-Compound II of 81% was obtained.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:
1. A method of bisformylating an arylamine, comprising reacting and refluxing an acidic solution comprising an arylamine compound with from about two to about 200 molar equivalents of an alkyleneamine to form a bisformylated arylamine.

2. A method in accordance with claim 1, wherein the arylamine compound is N,N-diphenyl-4-aminobiphenyl.

3. A method in accordance with claim 1 wherein said alkyleneamine contains from 1 to about 10 carbon atoms.

4. A method in accordance with claim 1 wherein said alkylene is methylene.

5. A method in accordance with claim 1, wherein the acidic solution further comprises an organic acid, an organic acid containing an inorganic acid, an organic solvent containing an organic acid, or an organic solvent containing an inorganic acid.

6. A method in accordance with claim 5, wherein the organic acid is at least one acid selected from the group consisting of acetic acid, propionic acid, trifluoroacetic acid, perfluoropropionic acid, methanesulfonic and perfluorobutanoic acid.

7. A method in accordance with claim 1, further comprising heating the acidic solution at a temperature ranging from about 70° C. to about 90° C.

8. A method in accordance with claim 1, wherein the alkyleneamine is hexamethylenetetraamine.

9. A method in accordance with claim 1, wherein reacting and refluxing occurs in a reaction mixture comprising from about 2 molar equivalents to about 10 molar equivalents of said acid.

10. A method of bisformylating an arylamine, comprising reacting an arylamine compound with an alkyleneamine in an acidic solution comprising paraformaldehyde and/or 1,3,5-trioxane to form a bisformylated arylamine.

11. A method in accordance with claim 10, wherein the paraformaldehyde or the 1,3,5-trioxane in the acidic solution is in a concentration ratio of from about 2 molar equivalents to about 40 molar equivalents of the arylamine.

12. A method in accordance with claim 10, wherein the arylamine is reacted with from about 15 to about 100 molar equivalents, of the alkyleneamine.

13. A method in accordance with claim 10, wherein the arylamine compound is N,N-diphenyl-4-aminobiphenyl.

14. A method in accordance with claim 10, further comprising heating the acidic solution at a temperature ranging from about 20° C. to about 120° C.

15. A method in accordance with claim 13, wherein the acidic solution is heated at a temperature ranging from about 70° C. to about 90° C.

16. A method in accordance with claim 10, wherein the alkyleneamine is hexamethylenetetraamine.

17. A method in accordance with claim 5, wherein the organic solvent is dimethylformamide or 1,4-dioxane, and the inorganic acid is hydrogen bromide or hydrogen chloride.

18. A method in accordance with claim 5, wherein the organic acid is at least one acid selected from the group consisting of acetic acid, propionic acid, trifluoroacetic acid, perfluoropropionic acid, methanesulfonic and perfluorobutanoic acid.

19. A method of purifying a solution containing bisformyl-arylamine and monoformyl-arylamine, comprising:
   (a) mixing an organic solution comprising bisformyl-arylamine and monoformyl-arylamine with a bisulfite solution to form a bisulfite salt, and
   (b) adding an organic solvent to the bisulfite salt, to form a purified bisformyl-araylamine.

20. A method in accordance with claim 19, wherein the bisulfite salt solution is saturated and comprises sodium bisulfite.

21. A method in accordance with claim 19, wherein the organic solvent is toluene.

* * * * *